(12) United States Patent
Ivanov

(10) Patent No.: US 8,558,791 B2
(45) Date of Patent: Oct. 15, 2013

(54) SENSOR SYSTEM FOR GENERATING SIGNALS THAT ARE INDICATIVE OF THE POSITION OR CHANGE OF POSITION OF LIMBS

(75) Inventor: Artem Ivanov, Gilching (DE)

(73) Assignee: Ident Technology AG, Wessling (DE)

( * ) Notice: Subject to any disclaimer, the term of this patent is extended or adjusted under 35 U.S.C. 154(b) by 314 days.

(21) Appl. No.: 12/682,303

(22) PCT Filed: Aug. 7, 2009

(86) PCT No.: PCT/EP2009/005754
§ 371 (c)(1),
(2), (4) Date: Jun. 14, 2010

(87) PCT Pub. No.: WO2010/015417
PCT Pub. Date: Feb. 11, 2010

(65) Prior Publication Data
US 2012/0313852 A1   Dec. 13, 2012

(51) Int. Cl.
*G06F 3/033* (2013.01)
*G06F 3/041* (2006.01)
*G01R 27/26* (2006.01)

(52) U.S. Cl.
USPC ............ 345/158; 345/173; 324/663; 324/678

(58) Field of Classification Search
USPC ................................................ 345/158–175
See application file for complete search history.

(56) References Cited

U.S. PATENT DOCUMENTS

| | | | |
|---|---|---|---|
| 5,844,415 A * | 12/1998 | Gershenfeld et al. | 324/663 |
| 2008/0018608 A1 * | 1/2008 | Serban et al. | 345/173 |
| 2008/0061800 A1 * | 3/2008 | Reynolds et al. | 324/678 |
| 2010/0001955 A1 | 1/2010 | Richter | 345/163 |
| 2012/0313852 A1 | 12/2012 | Ivanov | 345/158 |

FOREIGN PATENT DOCUMENTS

| DE | 202007017303 U1 | 4/2008 |
|---|---|---|
| WO | 2008/009687 A2 | 1/2008 |
| WO | 2010/015417 A2 | 2/2010 |

OTHER PUBLICATIONS

Chinese Office Action, Application No. 200980138720.1, 12 pages, Jan. 29, 2013.

* cited by examiner

*Primary Examiner* — Vijay Shankar
*Assistant Examiner* — Amit Chatly
(74) *Attorney, Agent, or Firm* — King & Spalding L.L.P.

(57) ABSTRACT

The invention relates to a sensor device for generating electronic signals which as such provide information on a position in space, and/or the movement of limbs, especially of the hand of a user in relation to the sensor device. Said electronic signals can be used to carry out input processes in data processing devices, communication devices and other electric devices. The aim of the invention is to devise ways of generating, in an especially advantageous manner, signals that are indicative of the position and/or the movement of limbs. A sensor device for generating electrical signals which as such provide information on the position or movement of limbs in relation to a reference area comprises a transmitter electrode device (G1, G1a, G1b), a voltage generator for supplying the transmitter electrode device (G1, G1a, G1b) with an alternating voltage of a first receiver electrode device, a second receiver electrode device, and a measurement circuit for detecting a field bridging effect towards the receiver electrode devices, said effect being correlated with a movement of the hand or the finger, a screening electrode device (S) at least substantially screening the transmitter electrode device (G1, G1a, G1b) and/or the receiver electrode device (M1, M2) from the measurement circuit with respect to field electrical effects.

10 Claims, 4 Drawing Sheets

SENSOR SYSTEM FOR GENERATING SIGNALS THAT ARE INDICATIVE OF THE POSITION OR CHANGE OF POSITION OF LIMBS

CROSS REFERENCE TO RELATED APPLICATIONS

This application is the US national phase of PCT application PCT/EP2009/005754, filed 7 Aug. 2009, published 11 Feb. 2010 as WO2010/015417, and claiming the priority of German patent application 102008036720.6 itself filed 7 Aug. 2008, whose entire disclosures are herewith incorporated by reference.

The invention relates to a sensor system for generating electronic signals indicating a three-dimensional position and/or the movement of limbs, in particular the hand of a user with respect to the sensor system. These electronic signals can then be used to carry out input processes in data-processing systems, communication devices and other electric devices. The sensor system according to the invention thus operates in this respect as a man/machine interface.

The invention is hence directed on a narrower scale at a gesture-detection system for the contactless detection of gestures, in particular hand or finger gestures in a capacitive manner. In particular, the invention is directed at a gesture-detection system that can be integrated into electronic devices in a simple manner. The object of the invention is thus to realize a relatively high-resolution gesture interface for control purposes, in particular of communication devices, as well as in the field of control panels and cockpit systems, which gesture interface is particularly reliable in terms of its function.

The object of the invention in this context is to create solutions for generating signals that indicate the position and/or the movement of limbs in a particularly advantageous manner.

This object is attained according to the invention through a sensor system according to claims 1.

It is thereby possible in an advantageous manner to provide the electronic circuit provided for generating the transmitter electrode field as well for evaluating the voltages detected by the sensor electrodes extremely close to the electrodes, with no field coupling that could distort the measurement signals between the sensor electrodes and the electronic circuit.

The "clover leaf" system according to the invention formed using a typically central transmitter electrode and at least three receiver electrodes arrayed around it provides a range and precision suitable for a typical hand movement area and thus suitable for many applications in the detection of gesture information.

With the concept according to the invention there are considerably reduced effects of grounding of any circuit components in the region of the circuit as well as also reduced interference between circuits of the device to be controlled per se.

The range of a capacitive detection system is essentially established by the area in which the electric field developed for detection purposes is present with sufficient (relative) strength. With the concept according to the invention, the effect is advantageously reduced that objects coupled to ground cause in the vicinity of the field-producing electrode, i.e. the field-generating electrode of the detection system, such that the electric field is strongly concentrated in the area between the electrode and the object. Accordingly, the detectable area is enlarged by the concept according to the invention. In particular in connection with the use of transimpedance wiring of the sensing electrodes, the influence of a virtual ground potential otherwise still present here is significantly reduced.

The electrode group ("clover leaf") provided with the detection system according to the invention is per se preferably embodied only with as little ground connection as possible. The optionally ground connected feed lines are preferably shielded. The sensing electrodes are preferably connected to the circuit in a high-impedance manner in order not to disturb the field distribution.

According to the invention, the measuring system is embodied such that the influence of the grounded parts (in particular its own circuitry) present in the region of the is measuring system is shielded from the transmitter electrode as well as the sensing electrodes arrayed around it and/or field bridging is compensated out.

Preferably the first, the second and the third receiver electrodes are connected to respective high-impedance inputs of an impedance-converter system, wherein the location-indicating or movement-indicating information is obtained based on differences between the electrical events at the respective outputs of the impedance converter.

A composite signal can be formed from the levels picked off the receiver electrodes, which composite signal shows the sum of the voltages applied at the receiver electrodes. This composite signal can be normalized with a predetermined amplification factor and made available to one respective comparator input of the impedance converter system.

Preferably, a synchronous detection system is provided that provides signals indicating synchronicity of the output signal at the respective impedance converter system, in particular with respect to voltage level and/or phase compared to the excitation voltage. Based on differences between the electrical events at the outputs of the synchronous detector, the location-indicating or movement-indicating information is obtained.

According to a particularly preferred embodiment of the invention, the receiver electrodes are arrayed symmetrically around the transmitter electrode. The transmitter electrode is preferably supplied with alternating voltage by a generator (microprocessor) and in order to form around it an electric field, preferably per se a quasistatic electric field. The receiver electrodes are preferably arrayed symmetrically around the transmitter electrode.

The electric voltage applied at the receiver electrodes contains information about the distribution of the field of the transmitter electrode.

The receiver electrodes are connected to the high-impedance inputs of the impedance converter in order not to disturb the electric field of the transmitter electrode. An average value is formed from the signals by the impedance converter. This average value can be amplified. The amplitude of this the amplified signals is determined by a synchronous detector and further digitalized by an ADC and transmitted to a microprocessor for evaluation. Instead of the synchronous detector, a diode rectifier or peak detector can also be used.

The sensor system according to the invention can be used in particular for detecting gestures, movements or hand positions. Preferably, at least the major part of the sensor circuitry including sensing electrodes is constructed in compact chip-like form. A particularly advantageous use of the sensor technology is hereby rendered possible.

With the concept according to the invention it is possible in an advantageous manner to create a large range for the detector for gestures, while the detector can be constructed in a compact manner. The concept according to the invention has, with detector dimension of 3.5 cm, a range of about 20 cm.

With the is circuit according to the invention the inputs are designed in a high-impedance manner. High-impedance inputs contribute in a surprisingly effective manner to enlargement of the range. This can be in particular visualized by a field simulation and generally reliably verified experimentally. According to the invention, for each channel the difference of its signal and of the average value is amplified. This makes it possible to achieve a high dynamic range with symmetrical electrodes or with signals made symmetrical in the circuitry even with simple ADCs (for example 10 bit). Very small signal changes can thereby be detected with simple means. The shielding electrode can also be acted on with a voltage which essentially has the same amplitude as the voltage applied at the transmitter electrode. The circuit can be such that it provides a relatively large number of electrodes, in particular 8 electrodes, i.e. 8 channels are realized. Apart from signal compensation by composite formation, a compensation by subtracting the weighted generator signals is also possible. This way the electrodes no longer need to be of equal size and no longer need to be arrayed symmetrically. The amplifiers can also be embodied as linear amplifiers. For shielding, the generator signal can be taken directly, i.e. not necessarily a signal that differs from it only in the amplitude.

Further details and features of the invention are given in the following description in connection with the drawing. Therein:

Figure 1:
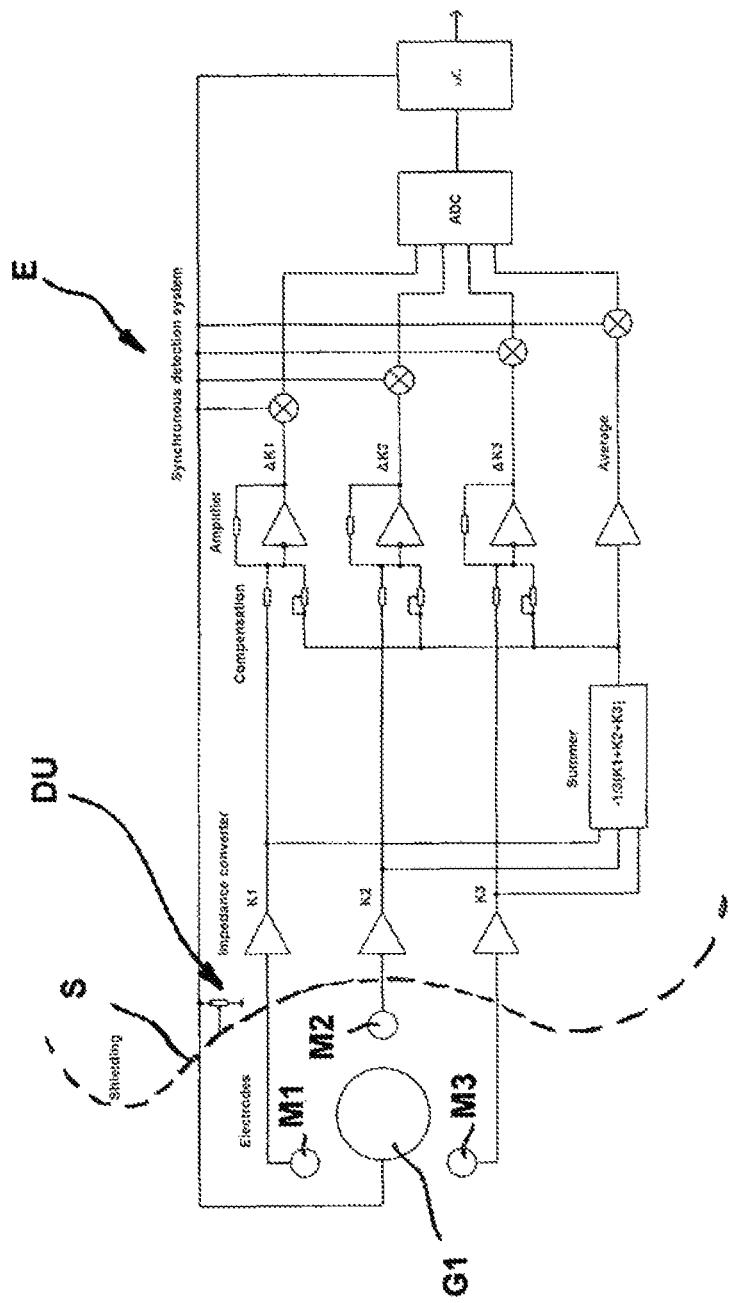
FIG. 1 is a block diagram showing the basic structure of a sensor system according to the invention.

As can be seen from the circuit diagram shown in FIG. 1, the system according to the invention can be realized with an assembly of plate electrodes that is shielded with respect to the actual circuit and drive circuit in the manner shown.

The electrodes are physically segregated from the rest of the circuitry. They can be for example traces on a printed-circuit board or conductive regions on a plastic film connected to the circuitry. Sensing electrodes M1, M2, M3 (2, 3, 4 or more) are arranged symmetrically around the transmitter electrode G1 (see for example for three electrodes in FIG. 2). The electrodes M1, M2, M3, G1 are connected to the circuitry E via thin conductive traces, so that the influence on the connections is as small as possible compared to that of the electrodes. The feeds can also be shielded in particular by for example a multilayer structure.

The influence of the circuitry of the detection system and of the device disturbing the field is minimized by shielding S. The shielding electrode S separates the electrode system M1, M2, M3, G1 from the circuitry E. This electrode [shield] S can for example be a plastic film with a conductive coating.

Figure 3:
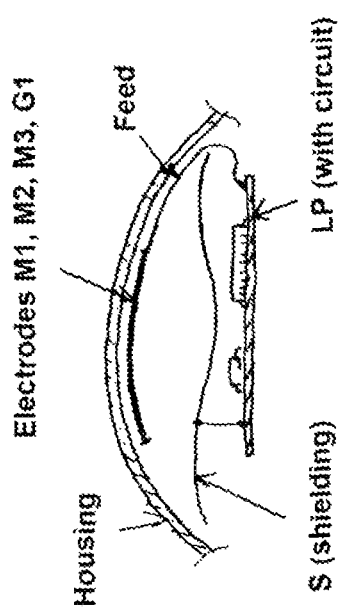
FIG. 3 is a sketch showing an exemplary arrangement of the transmitter electrode and the receiver electrode with a computer mouse forming a gesture interface.
Figure 4:
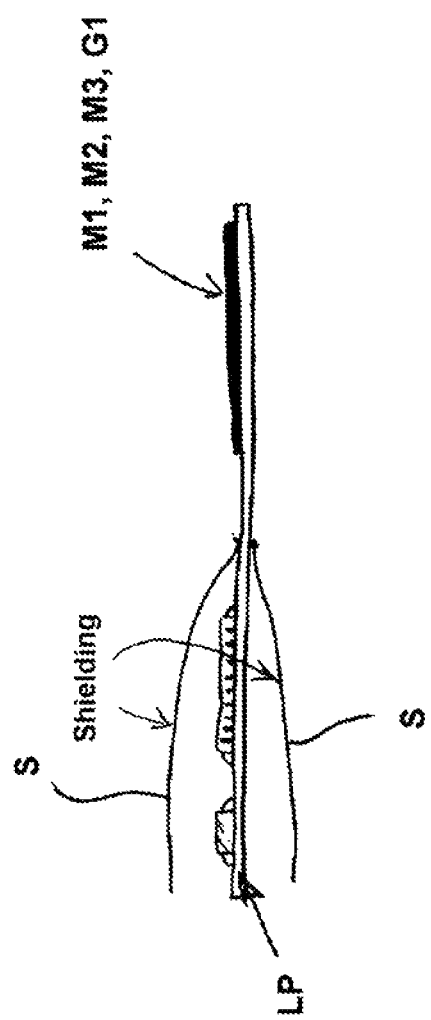
FIG. 4 is another sketch showing an exemplary arrangement of the transmitter electrode and the receiver electrode with a mobile communication device.

Examples of the three-dimensional embodiment are shown in FIGS. 3 and 4. The electrodes in FIG. 3 are attached to a plastic film via the printed-circuit board LP.

With the structure according to FIG. 4, the electrodes M1, M2, M3, G1 are integrated into the printed circuit as copper traces.

The shielding electrode S is acted on with a signal that differs only in amplitude from the signal on the transmitter electrode G1. This amplitude is selected such that the circuitry "concealed" behind the shielding electrode S is "camouflaged" from the electric field of the transmitter electrode G1. That means that the potential at the shielding electrode S corresponds to the potential generated by the transmitter electrode G1 at the same point if the circuitry and the shielding electrode were not present. The signal for the shielding electrode can be generated, for example, with the aid of an (adjustable) voltage divider DU from the signal of the transmitter electrode G.

The unavoidable quasistatic differences of the signals of the receiver electrodes M1, M2, M3 are compensated for electronically in the circuit. To this end, the composite signal formed is fed with different weighting to the amplifiers of individual channels (FIG. 1). The weighting is adjusted for each channel in order to keep the output signals of the amplifiers in the original state of the measuring system as close as possible to zero. This way, the best sensitivity for changes in the input signals is achieved with the (nonlinear) amplifiers.

Figure 2:
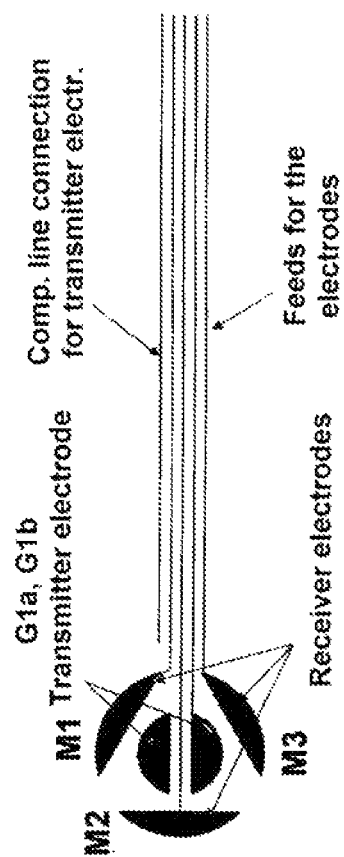
FIG. 2 is a schematic diagram showing an exemplary structure of the transmitter electrode and the receiver electrode.

The effectiveness of compensation is improved when the receiver electrodes have as far as possible the same coupling to the transmitter electrode. This coupling can be influenced, for example by additional electrodes:

FIG. 2 shows how an additional "balancing line" increases the coupling from the electrode M1 to a divided transmitter electrode G1$a$, G1$b$, namely to the level of the coupling of the electrodes M2 and M3.

The compensation can also be dynamically adjusted during operation in order to adjust the measuring system to any changing influences.

With the concept according to the invention it is possible to integrate the gesture-detection circuitry particularly advantageously directly into electronic devices, for example mobile phones. Furthermore, it is possible to integrate the electrodes directly into the printed-circuit board or to embody it as a conducting layer on a plastic film. Furthermore, it is possible to carry out the connection of the electrodes to the measuring system without coaxial cables. Through the concept according to the invention, furthermore, a maximization of the range of the detection system with given environment properties is achieved. In an advantageous manner, linearization of the system response to the is movement of the object to be detected also results.

The invention claimed is:

1. A sensor system for generating electrical signals indicating the position and/or the movement of limbs with respect to a reference area, the system comprising:
    a transmitter electrode,
    a voltage generator for applying an alternating voltage to the transmitter electrode and thereby creating an electric field around the transmitter electrode,
    a first receiver electrode in the field,
    a second receiver electrode in the field, and
    a detection circuit comprising high impedance inputs coupled with said first and second receiver electrode and being operable to detect a field-bridging effect caused by a hand or finger gesture and effective on the receiver electrodes, and
    a shielding electrode generally shielding the transmitter or the receiver electrode with respect to the detection circuit from the electric field, wherein a signal is fed to the shielding electrode which only differs in amplitude with respect to the alternating voltage applied to the transmitter electrode.

2. The sensor system according to claim 1, further comprising a third receiver electrode.

3. The sensor system according to claim 1 wherein the voltage generator only supplies said alternating voltage to said transmitter electrode and said shielding electrode.

4. The sensor system according to claim 1 wherein the first and second receiver electrodes are only connected to the high impedance input of the detection circuits.

5. The sensor system according to claim 1, wherein the amplitude is adjusted such that the circuit means arranged behind the shielding electrode is shielded from the electric field of the transmitter electrode.

6. The sensor system according to claim 1, wherein the amplitude is essentially adjusted such that a signal potential at the shielding electrode corresponds to a signal potential generated by the transmitter electrode at the same location if the circuit means and the shielding electrode were not present.

7. The sensor system according to claim 6, wherein the signal for the shielding electrode is generated with the aid of a dynamically adjustable voltage divider from the signal of the transmitter electrode.

8. The sensor system according to claim 1 wherein quasi-static differences of the signals of the receiver electrodes occurring are electronically compensated in the circuit means.

9. The sensor system according to claim 8, wherein each receiver electrode is assigned to an individual channel and a composite signal is formed and fed with different weighting to amplifiers of individual channels.

10. The sensor system according to claim 9, wherein the weighting is adjusted for each channel in order to keep the output signals of the amplifiers in the original state of the measuring system as close to zero as possible.

* * * * *

UNITED STATES PATENT AND TRADEMARK OFFICE
CERTIFICATE OF CORRECTION

PATENT NO.        : 8,558,791 B2                                Page 1 of 1
APPLICATION NO.   : 12/682303
DATED             : October 15, 2013
INVENTOR(S)       : Artem Ivanov It is certified that error appears in the above-identified patent and that said Letters Patent is hereby corrected as shown below:

Title Page:
Item (30), Foreign Application Priority Data is missing, should read
"Aug. 7, 2008   (DE) .................. 102008036720.6"

Signed and Sealed this
Seventeenth Day of December, 2013

Margaret A. Focarino
*Commissioner for Patents of the United States Patent and Trademark Office*